(12) United States Patent
Takahashi

(10) Patent No.: US 6,424,149 B1
(45) Date of Patent: Jul. 23, 2002

(54) NONDESTRUCTIVE FATIGUE TEST METHOD FOR FERROMAGNETIC CONSTRUCTION MATERIALS

(75) Inventor: Seiki Takahashi, Morioka (JP)

(73) Assignee: Iwate University, Morioka (JP)

( * ) Notice: Subject to any disclaimer, the term of this patent is extended or adjusted under 35 U.S.C. 154(b) by 0 days.

(21) Appl. No.: 09/706,108

(22) Filed: Nov. 3, 2000

(30) Foreign Application Priority Data

Nov. 8, 1999 (JP) ............................................. 11-316851

(51) Int. Cl.$^7$ ......................... G01R 33/14; G01R 33/16; G01R 33/18; G01B 7/24; G01N 27/72
(52) U.S. Cl. ........................ 324/209; 324/223; 73/760; 73/779
(58) Field of Search .................................. 324/201, 209, 324/222, 223, 239; 73/760, 779

(56) References Cited

U.S. PATENT DOCUMENTS

| | | | | |
|---|---|---|---|---|
| 3,925,725 A | * | 12/1975 | Mogilevsky et al. | ... 324/223 X |
| 4,316,146 A | * | 2/1982 | Jilken | .......................... 324/209 |
| 5,008,621 A | * | 4/1991 | Jiles | ........................ 324/223 X |
| 5,195,377 A | * | 3/1993 | Garshelis | ...................... 73/779 |
| 5,619,135 A | * | 4/1997 | Kohn et al. | ............. 324/209 X |
| 6,345,534 B1 | * | 2/2002 | Takahashi | ..................... 73/760 |

* cited by examiner

*Primary Examiner*—Gerard R. Strecker
(74) *Attorney, Agent, or Firm*—Knobbe, Martens, Olson and Bear, LLP.

(57) ABSTRACT

A nondestructive test method determines the degree of metal fatigue of test ferromagnetic construction materials by quantifying a change in effective stress due to aging of the test materials. The disclosed method is to measure the coercive force Hc and the magnetic susceptibility $\chi_H$ of the test materials at the field of the coercive force Hc. A current tensile stress $\sigma$ by putting the coercive force Hc and the magnetic susceptibility $\chi_H$ into the following first equation:

$$\sigma = a(Hc/\chi_H)^n.$$

where a and n are known constants determined by the internal structure of the test materials. A change in current tensile stress of the test materials is determined by comparing the effective tensile stress $\sigma$ of the test materials with the initial tensile stress $\sigma_0$ of the test materials.

8 Claims, 12 Drawing Sheets

NONDESTRUCTIVE FATIGUE TEST METHOD FOR FERROMAGNETIC CONSTRUCTION MATERIALS

BACKGROUND OF THE INVENTION

1. Field of the Invention

The present invention relates to a nondestructive test method for quantitatively determining fatigue of ferromagnetic construction materials, or of the structure comprised of such materials.

2. Description of the Related Art

Conventional nondestructive test methods for determining fatigue of materials are generally based on investigation of generation and growth of cracks in the material, and thus, it is highly important to find out as minute cracks as possible. With such a conventional nondestructive test method, it is practically impossible to evaluate metal fatigue of the material before cracks are generated.

There are also other types of nondestructive fatigue test methods known, which can be applied to ferromagnetic construction materials or structures comprised of such construction materials. One of such test methods is for measurement of the coercive force, and another method is for measurement of the magnetic susceptibility of the test material in the range approaching to saturation. It is known that the former method has less measurement sensitivity than the latter method, and such measurement sensitivity of the former method degrades when the materials that have more progressed metal fatigue are measured.

SUMMARY OF THE INVENTION

It is therefore a primary object of the present invention to provide an improved test method for nondestructively determining the metal fatigue of ferromagnetic construction materials, which advantageously eliminates the above-mentioned problems of the prior art.

One aspect of the present invention resides in a method for nondestructively determining metal fatigue of test ferromagnetic construction materials having a known, initial tensile stress $\sigma_0$, by quantifying a change in effective stress due to aging of the materials. The test method according to the present invention comprises the following three steps.

The first step is to measure the coercive force ($H_c$) and the magnetic susceptibility ($\chi_H$) of a test material under a magnetic field having a coercive force($H_c$).

The second step is to determine an effective tensile stress ($\sigma$) by putting said coercive force ($H_c$) and said magnetic susceptibility ($\chi_H$) into a following first equation:

$$\sigma = a(H_c/\chi_H)^n \quad (1)$$

where a and n are known constants determined by the internal structure of the test material.

Finally, the third step is to determine a change in effective tensile stress of the test material, by comparing said effective tensile stress ($\sigma$) of the test material with the initial tensile stress ($\sigma_0$) of the test material.

Another aspect of the present invention resides in an apparatus for nondestructively determining metal fatigue of test ferromagnetic construction materials having a known, initial tensile stress ($\sigma_0$), by quantifying a change in the effective stress due to aging of the test materials. The apparatus according to the present invention comprises:

i) measuring means for measuring the magnetic susceptibility ($\chi_H$) of a test material in its aged state, under a magnetic field having a coercive force (Hc);

ii) stress calculation means for calculating and thereby determining an effective tensile stress ($\sigma$) of the test material, by putting said coercive force ($H_c$) and said magnetic susceptibility ($\chi_H$) into a following first equation:

$$\sigma = a(H_c/\chi_H)^n \quad (1)$$

where a and n are known constants determined by the internal structure of the test material; and iii) evaluation means for determining a change in the effective stress of the test material due to aging thereof, by comparing the current tensile stress ($\sigma$) of the test material with its initial tensile stress ($\sigma$).

The nondestructive test apparatus according to the present invention, as a whole, may be comprised of a personal computer installed with programs based on the algorithm which enables execution of the above steps.

The principle of the present invention will be described below with reference to the experimental test data. To elucidate the interrelationship between the mechanical and magnetic properties of steel materials, test materials were prepared which consist of a pure iron single crystal, polycrystalline pure iron, and low-alloy steel A533B, respectively. These test materials were formed into samples having shapes as shown in FIGS. 1(a), 1(b) and 1(c), respectively, which are to be subjected to tensile and hysteresis loop tests. The samples as shown in FIG. 1(a) were used for the tensile test, while the samples as shown in FIG. 1(b) or 1(c) were used for the hysteresis loop test. As for the hysteresis loop test, the polycrystalline pure iron and low-alloy steel A533B took the shape of FIG. 1(b) while the pure iron single crystal took the shape of FIG. 1(c). Table 1 below shows the chemical composition of the low-alloy steel A533B submitted to the test.

TABLE 1

| A533B | C | Si | Mn | P | S | Cu | Ni | Mo | Al |
|---|---|---|---|---|---|---|---|---|---|
| Wt. % | 0.18 | 0.15 | 1.5 | 0.004 | 0.001 | 0.03 | 0.66 | 0.56 | 0.01 |

FIGS. 2 to 4 illustrate the stress-strain characteristics of the test samples, obtained from the tensile test. FIG. 2 represents the results from Fe single crystal samples, and shows that the strain rate (i.e., extension rate) is 1.5%/min. FIG. 3 represents the results from Fe polycrystalline samples, and shows that the strain rate is 1.2%/min, and FIG. 4 represents the results from a low-alloy steel A533B sample, and shows that the strain rate is 1.2%/min.

FIGS. 5 and 6 illustrate the magnetization curves obtained from the hysteresis loop test after the application of stresses. FIG. 5 shows the hysteresis loop characteristics of Fe single crystal samples with plastic deformation of stresses (0 MPa, 55 MPa, or 115 MPa), while FIG. 6 shows the hysteresis loop characteristics of Fe polycrystalline samples with plastic deformation of stresses (0 MPa, 550 MPa, or 663 MPa). The applied stresses were chosen to be equal to 0 MPa and the stress that develops just before fracture, both of which had been obtained from a preparatory tensile test, and the above mentioned intermediate stresses had been chosen between these values for plastic deformation.

From the magnetization curve of test materials as depicted in FIGS. 5 and 6, it is possible to determine the coercive force Hc (the magnetic field intensity H at the flux density B=0) of the individual test material related to the tensile stress σ. FIG. 7 is obtained when the coercive force Hc is plotted against the tensile stress σ. The solid triangles (▲), solid circles (●) and solid diamonds (♦) represent the results obtained from Fe single crystal material, Fe polycrystalline material, and low-alloy steel material, respectively.

Moreover, from the gradient of the magnetization curve of test materials near the flux density B=0 as depicted in FIGS. 5 and 6, it is possible to determine the magnetic susceptibility (H corresponds to the coercive force Hc). Thereby, FIG. 8 is obtained when a ratio of the coercive force Hc and the magnetic susceptibility $\chi_H$ at Hc, A=Hc/$\chi_H$ is calculated, and the logarithmic values of A are plotted in relation to corresponding logarithmic values of the tensile stress $\sigma$. The solid triangles (▲), solid circles (●) and solid diamonds (♦) represent the results obtained from Fe single crystal material, Fe polycrystalline material, and low-alloy steel material, respectively.

From FIG. 8, the inventor investigated that the relation of the tensile stress $\sigma$ and the value A is expressed by the following equation:

$$\log(\sigma) = \log(a) + n\log(A) \quad (2),$$

where $A = H_c/\chi_H$.

That is, the equation (2) can be expressed by the same form of the equation (1) as follows:

$$\sigma = a(A)^n \quad (3)$$

where the constants a and n are determined from the crystal structure of test materials. It is supposed that the single crystal pure iron, polycrystalline pure iron, and low-alloy A533B steel submitted to the test each has the body-centered cubic (BCC) lattice structure, and contains iron atoms as main ingredient, thus, the characteristics obtained with respect to those materials can be represented by a relevant equation which is expressed by the equation (3).

Thus, if the tensile stress a is unknown, by calculating the ratio A and substituting this value A to the equation (3), the tensile stress $\sigma$ can be obtained. This tensile stress a becomes a parameter of the mechanical strength of materials.

Moreover, the ratio A can be obtained by measuring the hysteresis loop nondestructively using the magnetic yoke which is provided coils or the coils provided on the test materials.

Therefore, with the method according to the present invention, it is possible precisely to determine the current stress of test materials by obtaining the coercive force Hc and the magnetic susceptibility $\chi_H$ corresponding to said Hc, and calculating the effective tensile stress $\sigma$ of the test materials by putting the value A which is the ratio of the coercive force Hc and the magnetic susceptibility $\chi_H$ into the equation which includes the known constants a and n termined by the internal structure of the materials:

$$\sigma = a(A)^n \quad (3),$$

and by comparing the current tensile stress a of the test material with its initial tensile stress $\sigma_0$.

It is to be noted that when construction materials are aged, i.e., exposed to a stress over a long period, lattice defects, such as dislocations develop; and the effective stress of the material increases. In this context, the increased effective stress of the test materials in their aged state is the current stress of the materials.

Moreover, in the conventional fatigue test method, the metal fatigue of test materials is evaluated by measuring the coercive force and obtaining the relation between the coercive force and the effective tensile stress, so that as shown in FIG. 7, the values of the coercive force only changes several tens times between the minimum and the maximum values of the tensile stress. On the other hand, the test method according to the present invention determines metal fatigue of test materials based on the relation between the effective stress a and the value A which is the ratio of the coercive force Hc and the magnetic susceptibility $\chi_H$ allowing the value A changes to be about 8000 times from $2.3 \times 10^{-6}$ to $1.8 \times 10^{-2}$ between the maximum and minimum of the tensile stress a, as seen from Table 2. Thus, as shown in FIG. 8, the range of the value for evaluation is expanded. This indicates that the method according to the present invention is more significantly sensitive to change in the tensile stress, which serves as a parameter for evaluating metal fatigue of test materials.

TABLE 2

| Test materials | Tensile stress $\sigma$ (MPa) | Coercive force Hc (Oe) | Magnetic susceptibility $\chi_H$(Gauss/Oe) | A(Hc/$\chi_H$) |
|---|---|---|---|---|
| Single crystal pure iron | 0 | 0.24 | 102450 | $2.3 \times 10^{-6}$ |
| A533B steel | 663 | 13.74 | 765.78 | $1.8 \times 10^{-2}$ |

FIG. 9 shows the relation of tensile stress a and the dislocation density $\rho$ based on the experiment. In this experiment, the hysteresis characteristic test is carried out for the test pieces after loading the tensile stress as shown in FIGS. 5 and 6, and the dislocation density of the test pieces is measured via the observation by means of electron microscope about each tensile stress. In FIG. 9, solid triangles (▲), solid circles (●) and solid diamonds (♦) represent the results obtained from Fe single crystal material, Fe polycrystalline material, and low-alloy steel material, respectively. From the experimental result, it is noted that there is a simple relation between tensile stress and the dislocation density. It is well-known that there is a certain relation between the dislocation density and metal fatigue. Therefore, from the above-mentioned experimental results, if the effective tensile stress is ascertained, it is possible to obtain the degree of metal fatigue from the tensile stress nondestructively.

Therefore, the method according to the present invention can be applied to the measurement of polycrystalline ferromagnetic construction materials and low-alloy steel materials. With this method, it is possible to examine the dislocation density and its distribution even before occurrence of cracks in the material nondestructively, and also to measure the degree of metal fatigue of the materials if the measurement is performed to fatigued ferromagnetic construction material.

In the nondestructive test method according to the present invention, the initial tensile stress $\sigma_0$ of test materials may be obtained from the following equation:

$$\sigma_0 = F/S \quad (4)$$

where F represents a force applied to test ferromagnetic construction materials, and S the sectional area of materials normal to the direction of the force. In this instance, assuming that the external and/or internal forces applied to test materials are known, the initial tensile stress $\sigma_0$ can readily be derived from the equation (4).

Alternatively, the aforementioned initial tensile stress $\sigma_0$ of test materials may be obtained from the equation (4) in the same manner as is in the effective tensile stress $\sigma$. In this instance, even when the external and/or internal forces applied to test materials are unknown, the initial tensile stress $\sigma_0$ can readily be derived as is the case with the current tensile stress $\sigma$.

Still further, in the nondestructive test method according to the present invention, a U-shaped magnetic yoke may be used for measuring the coercive force Hc of test ferromagnetic construction materials. It is then possible to perform a nondestructive measurement on the test materials having a shape which does not readily permit a coil to be wound around them.

Moreover, in this invention, it is possible to construct the apparatus for nondestructively determining metal fatigue of test ferromagnetic construction materials by combining the means which perform aforementioned each step of the method according to this invention. To put it concretely, this apparatus may comprises:

i) measuring means for measuring the magnetic susceptibility ($\chi_H$) of test material in its aged state, under a magnetic field having a coercive force ($H_c$);

ii) stress calculation means for calculating and thereby determining an effective tensile stress ($\sigma$) of the test material, by putting said coercive force $H_c$ and said magnetic susceptibility ($\chi_H$) into a following first equation:

$$\sigma = a(H_c/\chi_H)^n \quad (1)$$

where a and n are known constants determined by internal structure of the test material; and iii) evaluation means for determining a change in effective stress of the test material due to aging thereof, by comparing the current tensile stress ($\sigma$) of the test material with its initial tensile stress ($\sigma_0$).

DESCRIPTION OF THE PREFERRED EMBODIMENTS

Figure 1A:
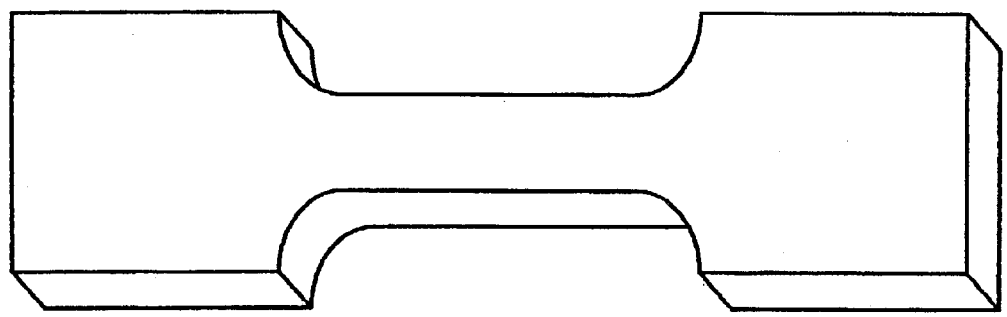
FIGS. 1a, 1b and 1c are views showing the shape of samples to be submitted to the tensile and hysteresis loop tests.
Figure 1B:
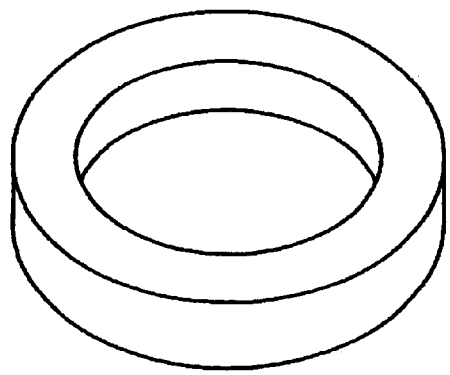
Figure 1C:
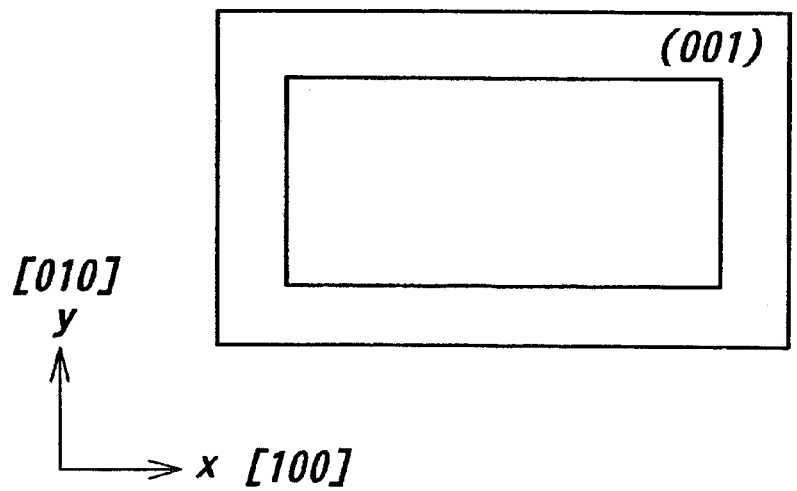
Figure 2:
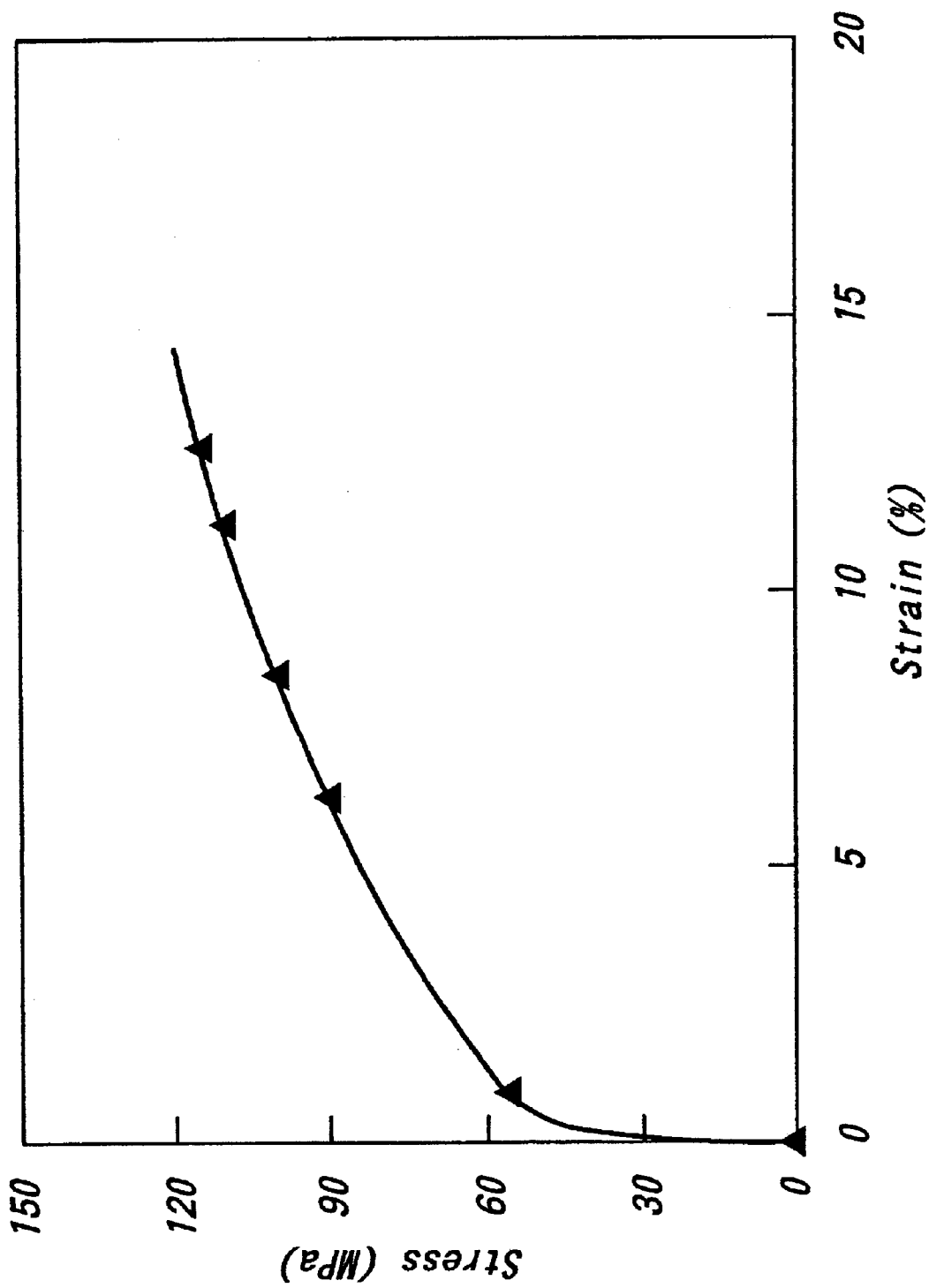
FIG. 2 is a stress-strain diagram of pure iron single crystal samples obtained from the tensile test.
Figure 3:
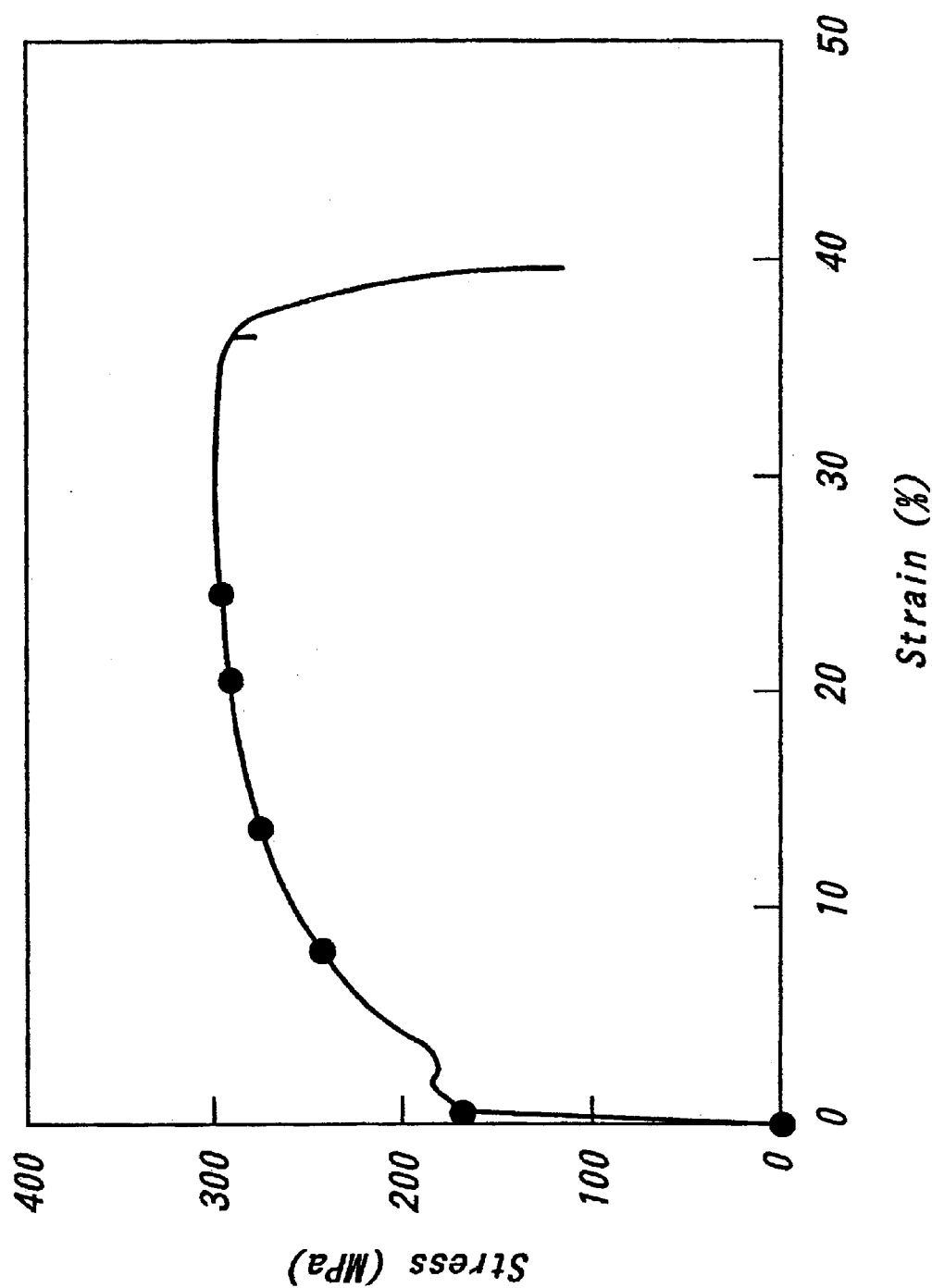
FIG. 3 is a stress-strain diagram of pure iron polycrystalline samples obtained from the tensile test.
Figure 4:
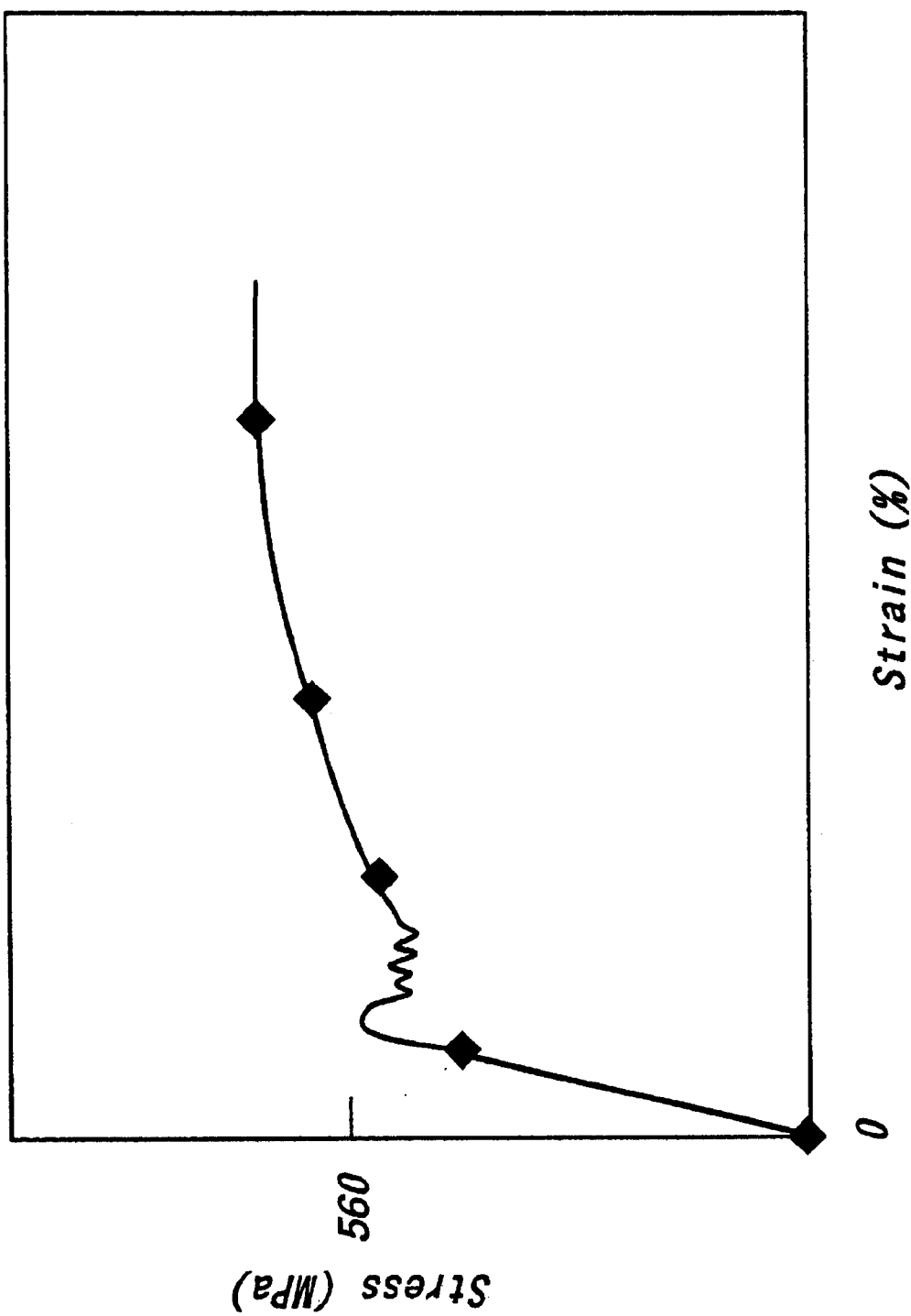
FIG. 4 is a stress-strain diagram of a low-alloy steel A533B samples obtained from the tensile test.
Figure 5:
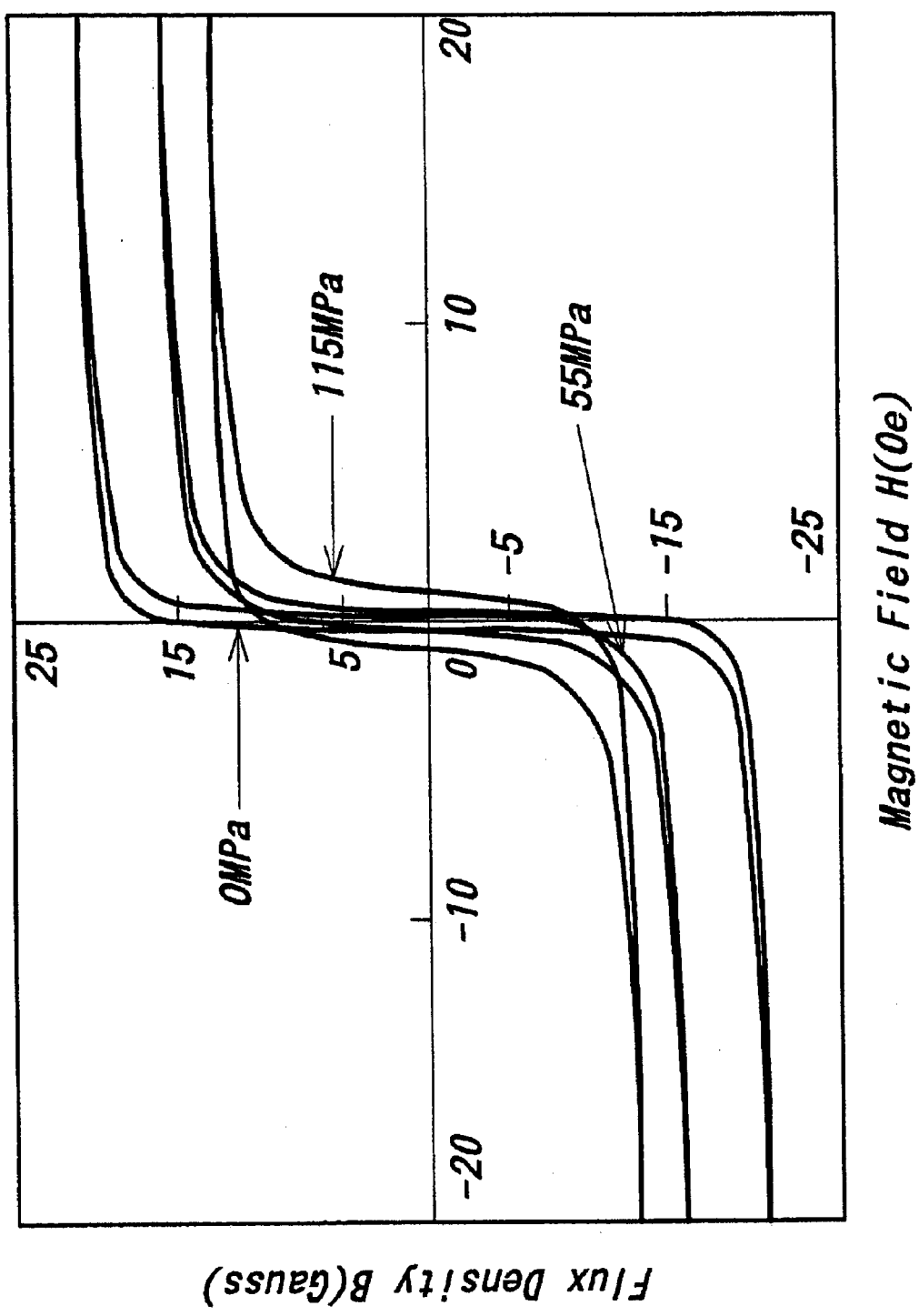
FIG. 5 is a graph showing the hysteresis characteristics of Fe single crystal samples under the stresses of 0 MPa, 55 MPa and 115 MPa, respectively.
Figure 6:
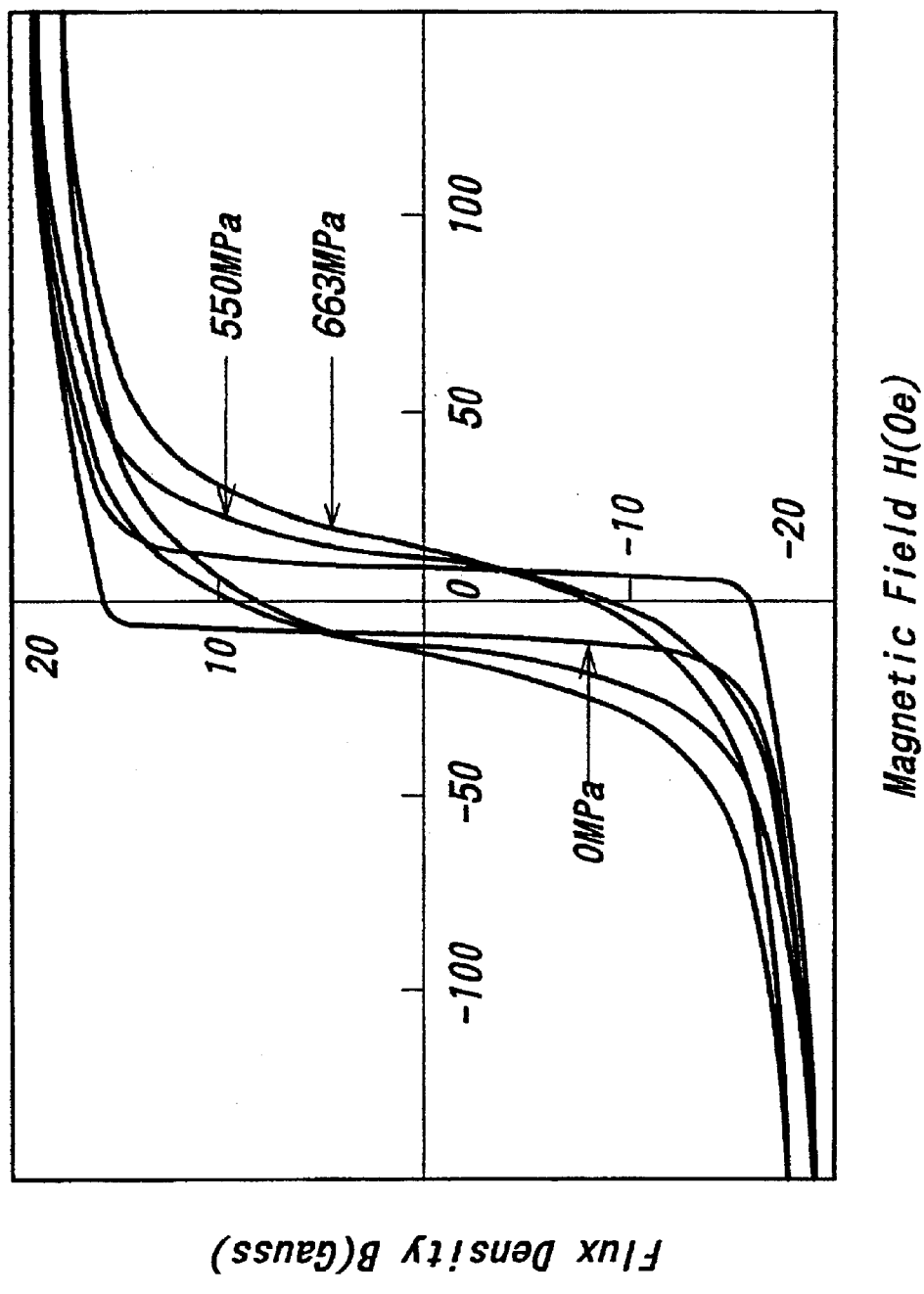
FIG. 6 is a graph showing the hysteresis characteristics of low-alloy steel A533B samples under the stresses of 0 MPa, 550 MPa and 633 MPa, respectively.
Figure 7:
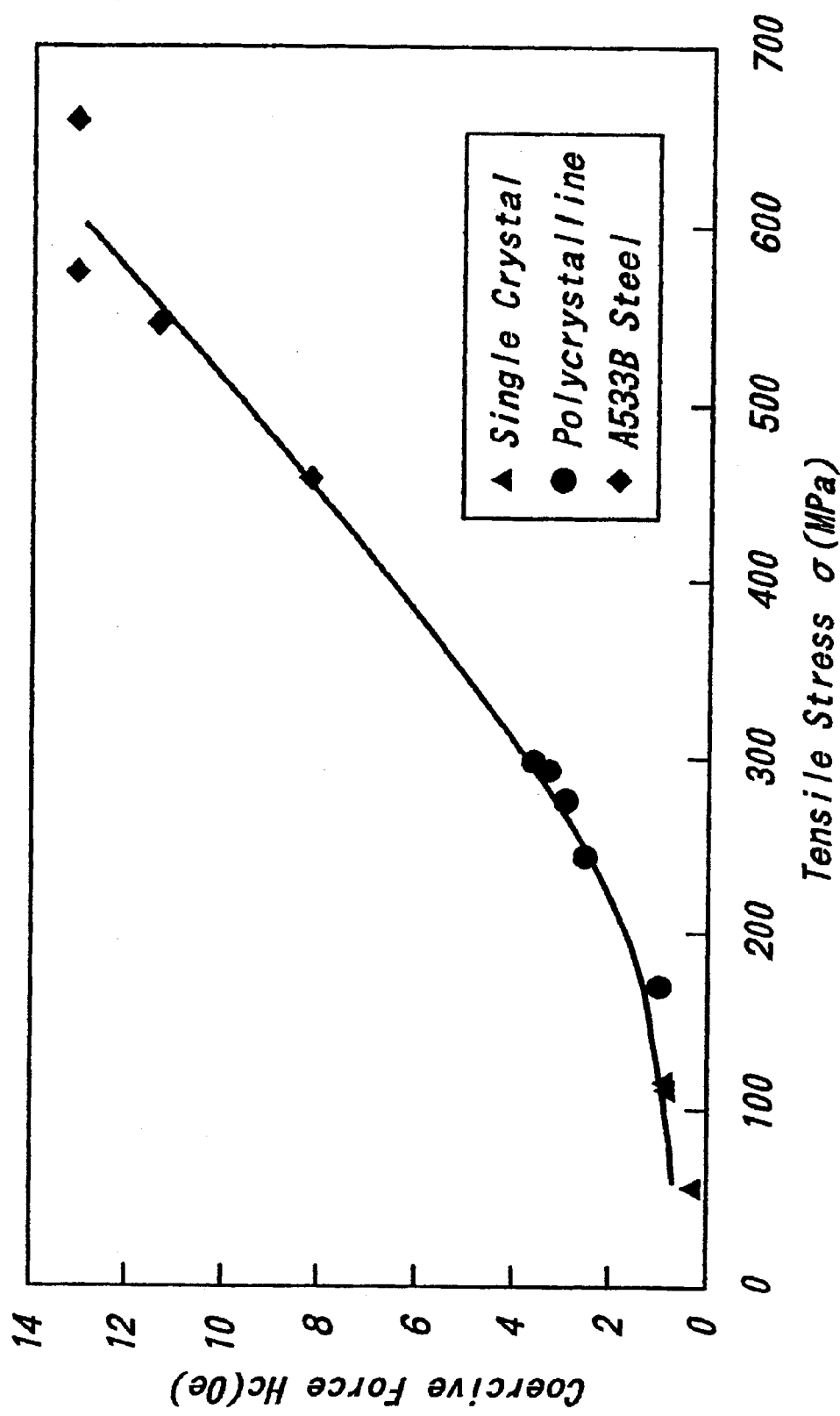
FIG. 7 is a graph showing the relation of the tensile stress $\sigma$ and the ratio A of the coercive force Hc and the magnetic susceptibility $\chi_H$ of the test materials from the experimental results.
Figure 8:
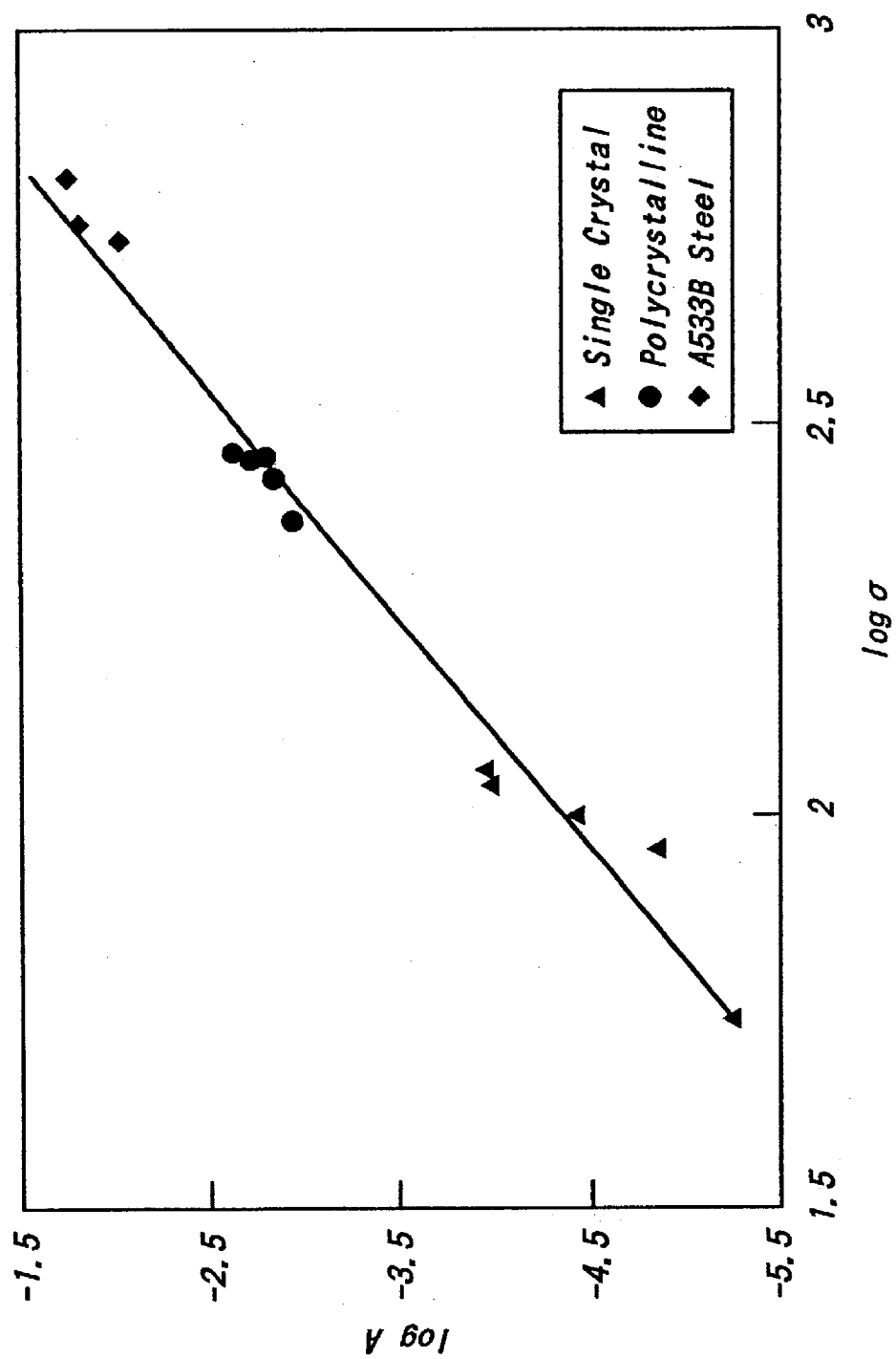
FIG. 8 is a graph showing the relation of the logarithmic value of tensile stress log $\sigma$ and the logarithmic value of ratio A, the ratio between the coercive force Hc and the magnetic susceptibility $\chi_H$, log A in the test materials from the experimental results.
Figure 9:
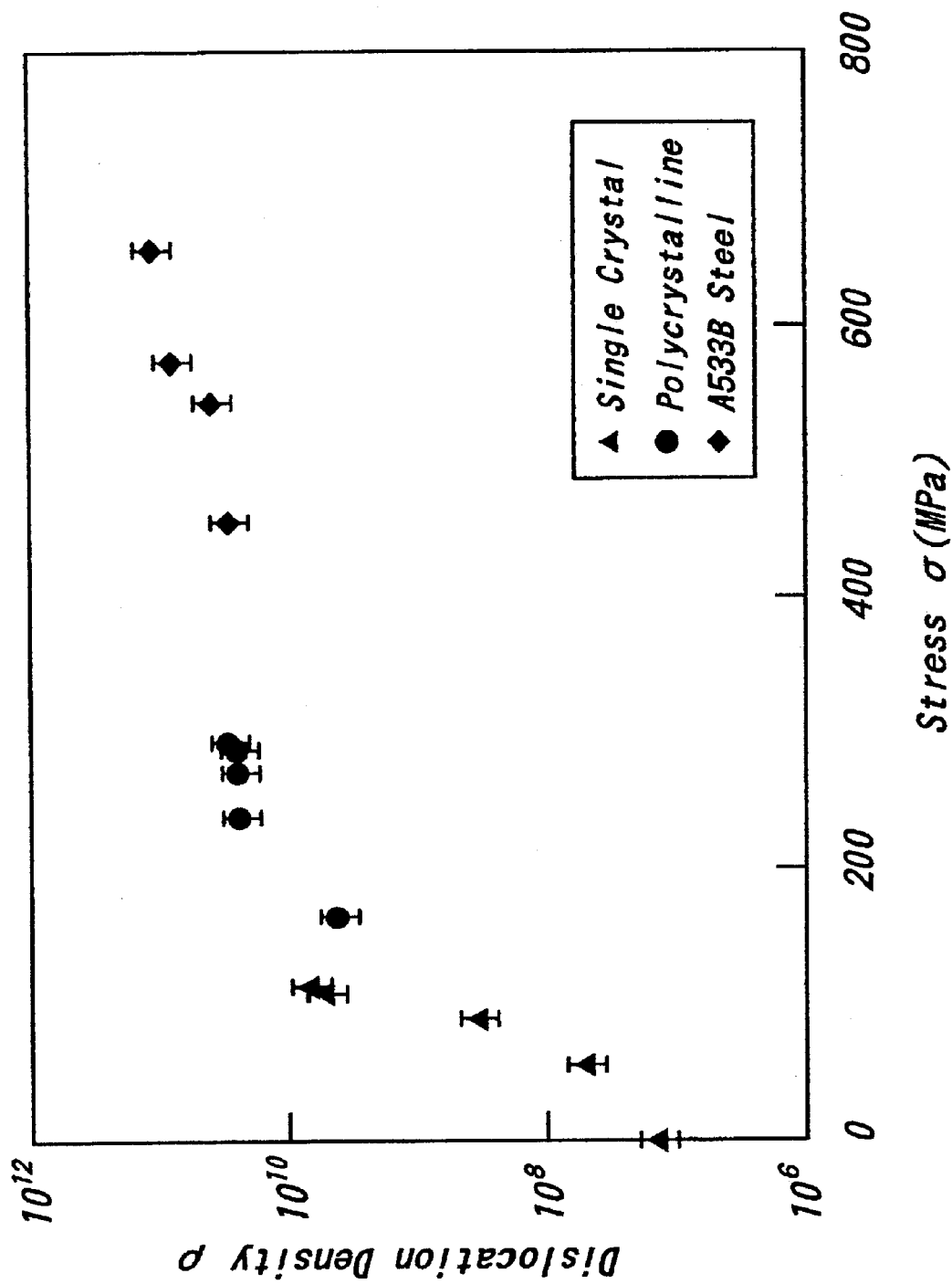
FIG. 9 is a graph showing the relation of the tensile stress $\sigma$ and the dislocation density $\rho$ of the test materials from the experimental results.
Figure 10:
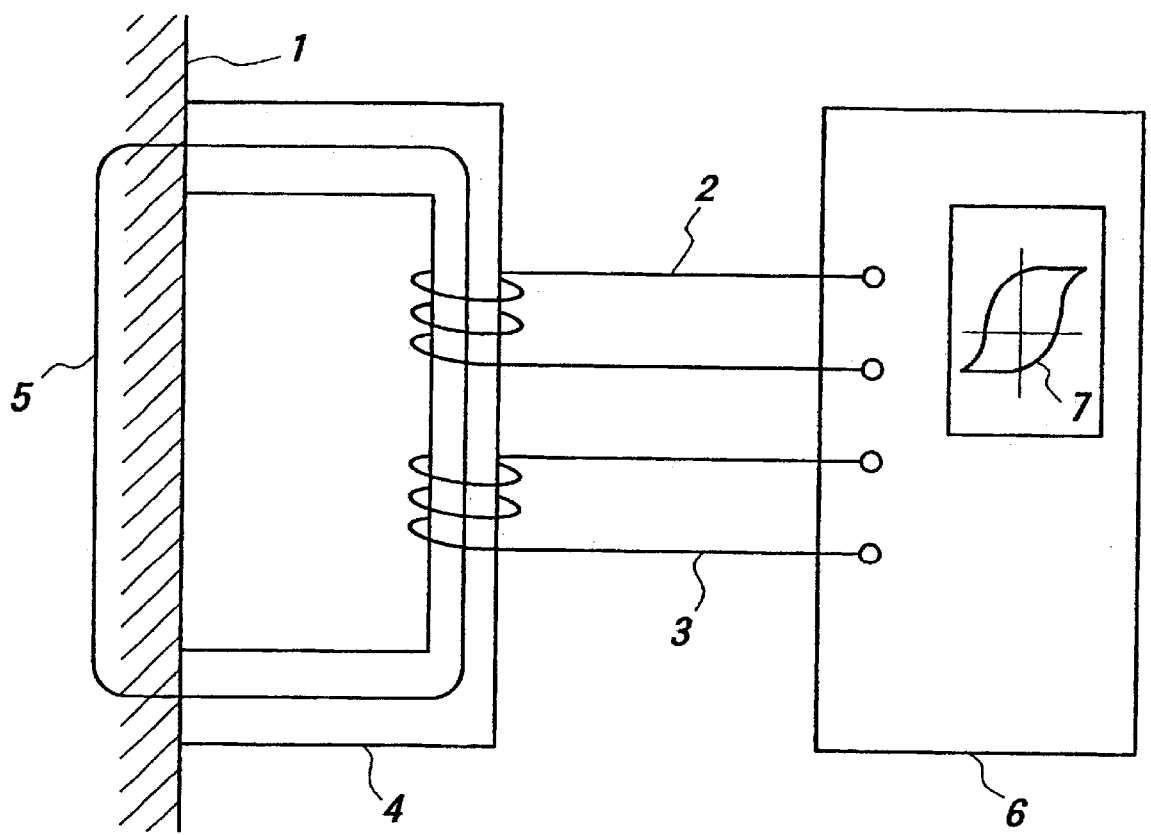
FIG. 10 is a schematic view showing one embodiment of the nondestructive fatigue test method according to the present invention as applied to determine metal fatigue of ferromagnetic construction materials.

The present invention will be described below in further detail, with reference to preferred embodiments shown in the attached drawings. FIG. 10 illustrates the first example of the nondestructive fatigue test method according to the present invention, wherein reference numeral 1 denotes a test structure comprised of ferromagnetic construction materials and exposed to external and/or internal forces; 2 a magnetizing coil; 3 a flux detecting coil; and 4 a magnetic yoke on which these coils 2, 3 are wound. As shown in FIG. 10, the test structure 1 has a shape for which a direct winding of the coils 2, 3 is impossible. Thus, the magnetic yoke 4 incorporating the magnetizing coil 2 and flux detecting coil 3 is tightly applied onto the test structure 1 to form a closed magnetic circuit 5. The magnetizing coil 2 and flux detecting coil 3 are connected to a magnetization measuring device 6. The magnetization measuring device 6 may be one which is commercially available in the market. The curve 7 represents the magnetization or a hysteresis loop of the test structure 1, which is determined by, and displayed on the magnetization measuring device 6.

In the test method according to the present invention, in order to perform a nondestructive fatigue test of the structure 1, the magnetization measuring device 6 supplies the magnetizing coil 2 with a magnetizing current. As a result, a voltage is induced in the flux detecting coil 3 and transmitted to the magnetization measuring device 6. The voltage is amplified and integrated by the measuring device 6 to determine the hysteresis loop 7 of the test structure 1.

The hysteresis loop 7 obtained from the measurement may contain errors due to the three dimensional expanse of the flux pathways in the ferromagnetic material of the test structure 1 and also due to the demagnetizing factor. To obtain the hysteresis loop characteristics free from such errors, it is necessary to determine the correction factors. The correction factors might be obtained by a computer experiment based on a known static magnetic field analysis, or by a mock-up experiment simulating the measurement system.

With the simulated hysteresis loop characteristics as explained above, the coercive force $H_c$ and the magnetic susceptibility $\chi_H$ which is the gradient of the curve of the hysteresis loop under a magnetic filed having a coercive force $H_c$ are measured. The value A which is the ratio between the coercive force $H_c$ and the magnetic susceptibility $\chi_H$, that is, $H_c/\chi_H$ is calculated from aforementioned $H_c$ and $\chi_H$. Then, the effective tensile stress $\sigma$ within the test material 1 exposed to external, and/or internal forces is determined by putting the ratio A into the equation (3):

$$\sigma = a(H_c/\chi_H)^n \quad (3)$$

The constants a and n in the equation (3) may be determined in advance by a preparatory test with respect to a test piece which is made of the same ferromagnetic material. When the values of a and n are put into the equation (3), the relation of the ratio A with the tensile stress σ is represented by the substantially straight calibration line 8 in FIG. 11. The effective tensile stress a of the test material corresponding to the ratio A can be readily determined from the calibration line 8.

It is necessary to determine the initial tensile stress $\sigma_0$ of the test ferromagnetic structure 1 at the initial phase because it serves as a reference for determining the current metal fatigue of the test material after it has been aged. When the direction and magnitude of the force applied to the ferromagnetic structure 1 are known, the initial tensile stress $\sigma_0$ can be obtained from the equation (4):

$$\sigma_0 = F/S \quad (4)$$

where F represents the intensity of the force, and S the sectional area of the test structure normal to the direction of the force.

On the contrary, when the direction and/or the magnitude of the force applied to the test structure 1 are unknown, it is still possible to determine the initial tensile stress $\sigma_0$ of the structure by using the above-mentioned equations (4) as in the case of the effective tensile stress σ.

The currently effective tensile stress σ obtained as above is compared with the initial tensile stress $\sigma_0$, and the difference δ between these stresses is used as a parameter which represents the fatigue of the test structure 1. It is thus possible to nondestructively determine the fatigue degree of a structure which is comprised of ferromagnetic materials.

Figure 11:
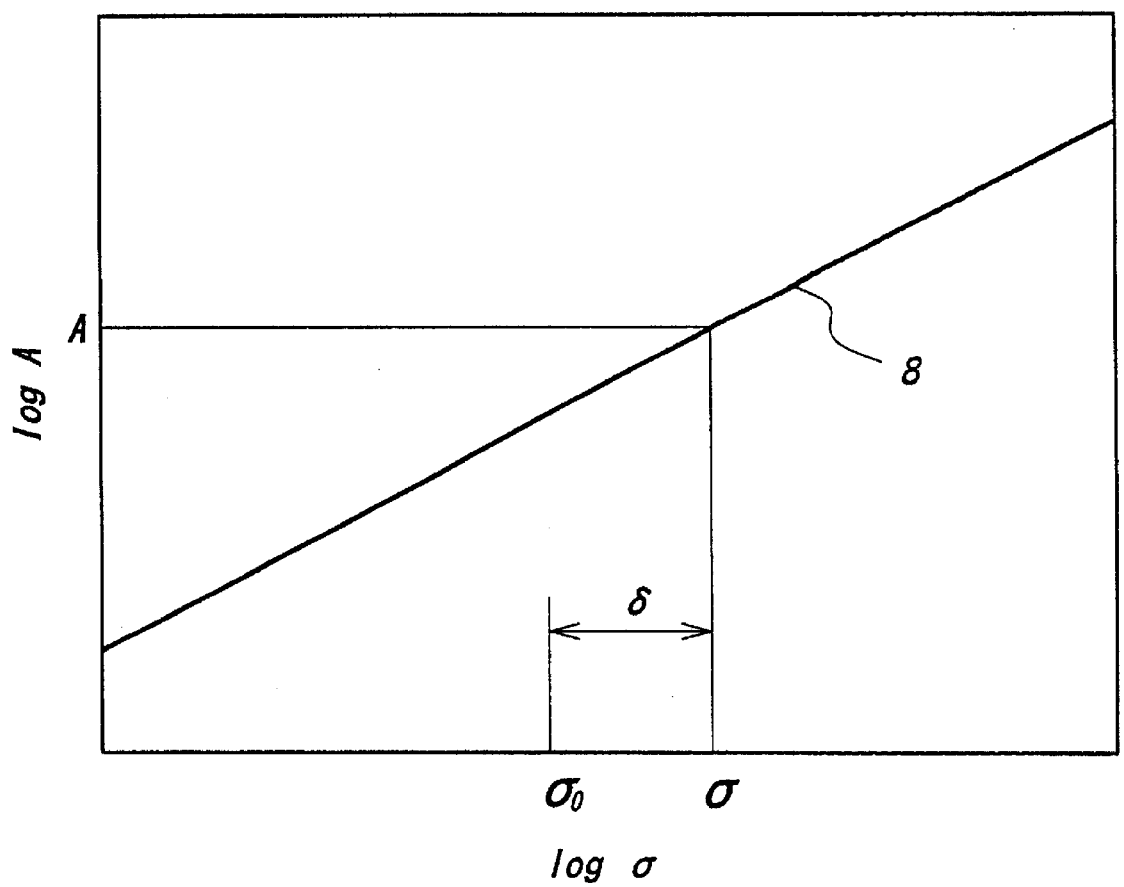
FIG. 11 is a graph which is used to determine the fatigue in the structure comprised of ferromagnetic construction materials, based on effective tensile stress $\sigma$ as computed from the ratio A of the coercive force. Hc and the magnetic susceptibility $\chi_H$.

Therefore, the nondestructive fatigue test method according to the illustrated embodiment makes it possible (i) to obtain a simulated hysteresis curve under a magnetic field of an intensity H that allows the measurement of coercive force Hc by measurement with an apparatus that includes a magnetic yoke and magnetizing power source, (ii) to calculate the ratio A of the coercive force Hc and the magnetic susceptibility $\chi_H$, precisely and nondestructively to determine the effective tensile stress a corresponding to the above ratio A on the calibration line 8 which represents the relation between the ratio A and the tensile stress as depicted in FIG. 11, (iii) to compare the current stress with the initial stress, and (iv) nondestructively to determine the metal fatigue degree of the test materials. Further, because the test method is applicable to low-alloy steels, it is possible precisely and nondestructively to determine the metal fatigue of any structure made of ferromagnetic construction materials, such as a pressure vessel of a nuclear reactor, before cracks are actually generated in the structure, by determining the density and distribution of dislocations, and also to measure the metal fatigue degree.

Figure 12:
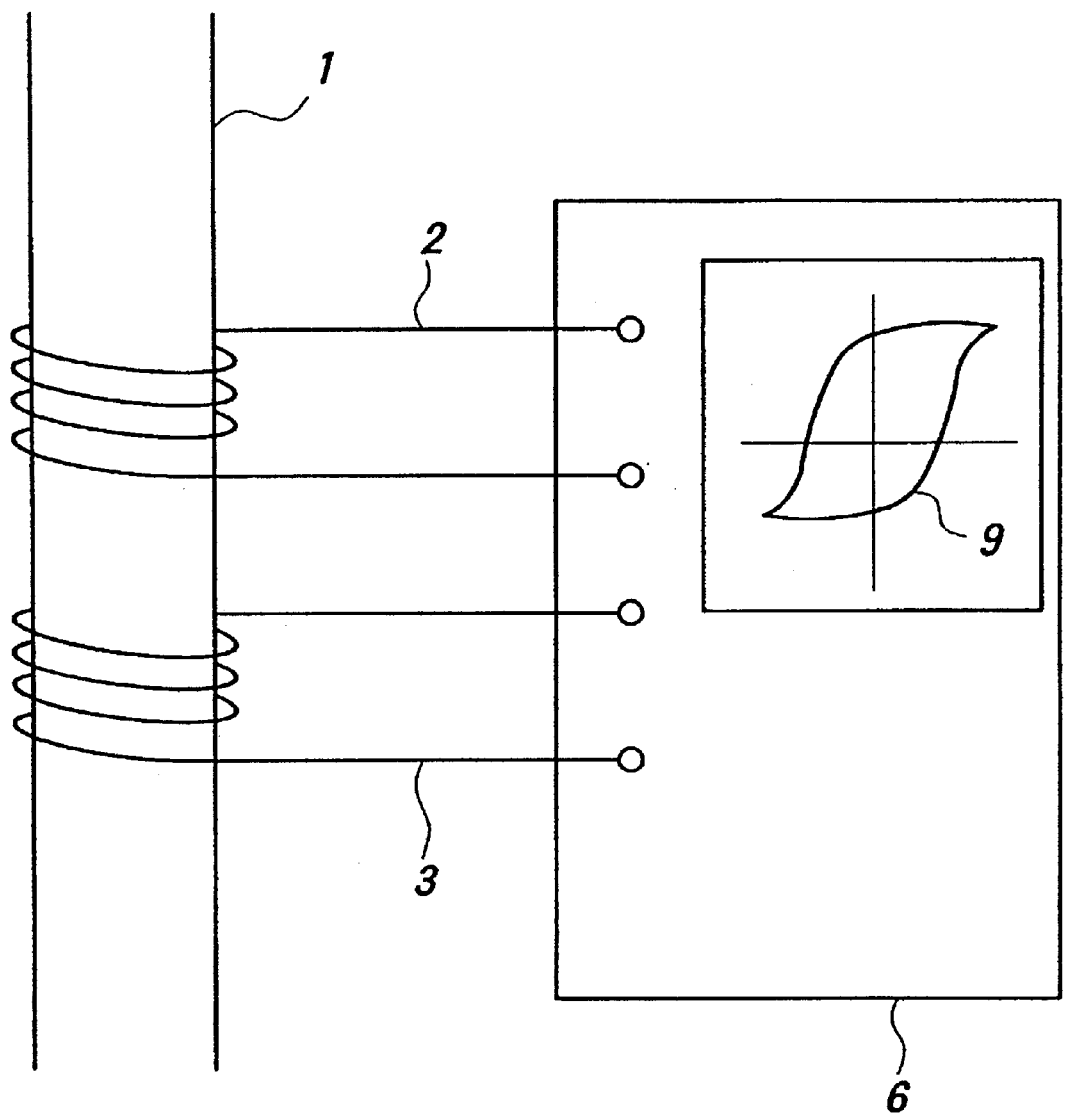
FIG. 12 is a schematic view showing another embodiment of the nondestructive fatigue test method according to the present invention as applied to determine fatigue of ferromagnetic construction materials.

FIG. 12 illustrates a second embodiment of the nondestructive fatigue test method according to the present invention which is also applied to determine the metal fatigue of ferromagnetic construction materials. In contrast to the above-mentioned first embodiment, the test structure 1 in the present embodiment has a shape which allows a magnetizing coil 2 and a flux detecting coil 3 to be directly wound thereon. Thus, the magnetizing coil 2 and the flux detecting coil 3 are wound on the test structure 1 and connected to the hysteresis loop determining device 6 which may be comprised of a commercially available product as in the first embodiment. The curve 9 represents the hysteresis loop of the test structure 1 which is determined by, and displayed on the hysteresis loop determining device 6 as a result of the test performed.

The second embodiment shown in FIG. 12 is similar to the first embodiment in that the ratio A of the coercive force Hc and the magnetic susceptibility $\chi_H$ is calculated from the hysteresis characteristics 9 obtained from a measurement, and the effective tensile stress σ is obtained from the ratio A. Then, the currently effective tensile stress σ of the test structure 1 can be compared with its initial tensile stress $\sigma_0$, and the difference between these stresses is used nondestructively to determine the fatigue of the test structure.

The nondestructive fatigue test method according to the second embodiment explained above achieves all of the functional advantages (i) through (iv) of the first embodiment. Additionally, the test method of the second embodiment makes it possible nondestructively to determine the fatigue degree of ferromagnetic construction materials without requiring a magnetic yoke, thereby making the entire system further simple in structure and light in weight.

The test apparatus suitable for carrying out the test method according to the present invention may be comprised of an appropriate work station or a personal computer incorporating programs based on the algorithms which is so prepared as to execute the above process steps.

While the present invention has been fully described above with reference to specific embodiments, they were presented solely for the purpose of illustration. Thus, a skilled person will readily appreciate that various changes or modifications may be made without departing from the scope of the invention as defined by the appended claims.

What is claimed is:

1. A method for nondestructively determining fatigue of test ferromagnetic construction materials having a known, initial tensile stress ($\sigma_0$), by quantifying a change in effective tensile stress due to aging of materials, said method comprising the steps of:

measuring a coercive force ($H_c$) and a magnetic susceptibility ($\chi_H$) of a test material under a magnetic field having a coercive force ($H_c$);

determining an effective tensile stress (σ) by putting said, coercive force ($H_c$) and said magnetic susceptibility ($\chi_H$) into the following first equation:

$$\sigma = a(H_c/\chi_H)^n$$

where a and n are known constants determined by an internal structure of the test material; and determining a change in effective tensile stress of the test material, by comparing said effective tensile stress (σ) of the test material with the initial tensile stress ($\sigma_0$) of the test material.

2. The test method according to claim 1, wherein said initial tensile stress ($\sigma_0$) of the test material is determined by putting a force (F) applied to the ferromagnetic construction material and the sectional area (S) of the test material normal to the direction of the force, into a second equation:

$$\sigma_0 = F/S.$$

3. The test method according to claim 1, wherein said initial tensile stress ($\sigma_0$) of the test material is determined in the same manner as the current tensile stress (σ) of the test material, by using said first equation.

4. The test method according to claim 1, wherein the coercive force (Hc) of the test ferromagnetic construction material is measured by using a magnetic yoke.

5. An apparatus for nondestructively determining the fatigue degree of a test ferromagnetic construction material having a known, initial tensile stress ($\sigma_0$), by quantifying a change in effective stress due to aging of the test material, said apparatus comprising:

measuring means for measuring the magnetic susceptibility ($\chi_H$) of a test material in its aged state, under a magnetic field having a coercive force ($H_c$);

stress calculation means for calculating and thereby determining an effective tensile stress ($\sigma$) of the test material, by putting said coercive force ($H_c$) and said magnetic susceptibility ($\chi_H$) into the following first equation:

$$\sigma = a(H_c/\chi_H)^n$$

where a and n are known constants determined by an internal structure of the test materials; and evaluation means for determining a change in effective stress of the test material due to aging thereof, by comparing the effective tensile stress ($\sigma$) of the test material with its initial tensile stress($\sigma_0$).

6. The apparatus according to claim 5, further comprising a magnetic yoke for measuring the coercive force (Hc) of the test material.

7. The test method according to claim 2, wherein the coercive force (Hc) of the test ferromagnetic construction material is measured by using a magnetic yoke.

8. The test method according to claim 3, wherein the coercive force (Hc) of the test ferromagnetic construction material is measured by using a magnetic yoke.

* * * * *